United States Patent
Zhu et al.

(10) Patent No.: US 10,414,756 B2
(45) Date of Patent: Sep. 17, 2019

(54) 2-(2,4,5-SUBSTITUTED ANILINE) PYRIMIDINE DERIVATIVE, PHARMACEUTICAL COMPOSITION AND USE THEREOF

(71) Applicant: Nanjing Diansu Biological Technology Co., Ltd., Nanjing, Jiangsu (CN)

(72) Inventors: Xiaoyun Zhu, Changzhou (CN); Mingyu Jiang, Changzhou (CN); Aining Ji, Changzhou (CN)

(73) Assignee: NANJING DIANSU BIOLOGICAL TECHNOLOGY CO. LTD, Jiangsu (CN)

( * ) Notice: Subject to any disclaimer, the term of this patent is extended or adjusted under 35 U.S.C. 154(b) by 0 days.

(21) Appl. No.: 15/553,892

(22) PCT Filed: Jul. 31, 2015

(86) PCT No.: PCT/CN2015/085714
§ 371 (c)(1),
(2) Date: Aug. 25, 2017

(87) PCT Pub. No.: WO2016/023422
PCT Pub. Date: Feb. 18, 2016

(65) Prior Publication Data
US 2018/0016258 A1  Jan. 18, 2018

(30) Foreign Application Priority Data
Aug. 15, 2014 (CN) .......................... 2014 1 0401604

(51) Int. Cl.
*C07D 403/04* (2006.01)
*C07B 59/00* (2006.01)
*A61K 31/506* (2006.01)

(52) U.S. Cl.
CPC .......... *C07D 403/04* (2013.01); *A61K 31/506* (2013.01); *C07B 59/002* (2013.01); *C07B 2200/05* (2013.01)

(58) Field of Classification Search
CPC .... C07D 403/04; C07B 59/002; A61K 31/506
See application file for complete search history.

(56) References Cited

FOREIGN PATENT DOCUMENTS

| CN | 103702990 A | * | 4/2014 |
| CN | 104140418 | * | 11/2014 |
| CN | 104140418 A |  | 11/2014 |
| JP | 2012502038 A |  | 1/2012 |
| WO | 2013014448 A1 | * | 1/2013 |

OTHER PUBLICATIONS

S.L. Harbeson et al., Deuterium in Drug Discovery and Development, in 46 Annual Reports in Medicinal Chemistry, 403-417 (2011).*

Oct. 30, 2015 International Search Report issued in International Patent Application No. PCT/CN2015/085714.
Oct. 30, 2015 Written Opinion of the International Searching Authority issued in International Patent Application No. PCT/CN2015/085714.
Nov. 4, 2015 Chinese Office Action issued in Chinese Patent Application No. 201410401604.7.
Apr. 24, 2017 Europe Office Action issued in Europe Patent Application No. 15832588.6 (ESR).
Nov. 29, 2017 Australian Office Action issued in Australian Patent Application No. 2015303641.
Jan. 19, 2018 Japanese Office Action issued in Japanese Patent Application No. 2015303641.
Science[2004], vol. 304, 1497-500.
New England Journal of medicine [2004], vol. 350, 2129-39.
R&D Systems DuoSet IC Human Phospho-EGF R ELISA(R&D systems, No.#DYC1095).
Shizhen Wang, Nuclear Medicine, Molecular Nuclear Medicine (Second Edition), Peking Union Medical College Press, Apr. 2004, p. 417-418.
Feb. 5, 2018 Europe Office Action issued in Europe Patent Application No. 15832588.6 (1st OA).
Kushner et al., Pharmacological uses and perspectives of heavy water and deuterated compounds, Can. J. Physiol Pharmacol. vol. 77, 1999, 79-88.

(Continued)

*Primary Examiner* — Alexander R Pagano
*Assistant Examiner* — Ebenezer O Sackey
(74) *Attorney, Agent, or Firm* — Harness, Dickey & Pierce, P.L.C.

(57) ABSTRACT

Disclosed are a 2-(2,4,5-substituted aniline) pyrimidine derivative, a pharmaceutical composition and a use thereof. The pharmaceutical composition comprises a therapeutically effective amount of the 2-(2,4,5-substituted aniline) pyrimidine derivative, a solvate, or a pharmaceutically acceptable salt thereof, and a pharmaceutically acceptable excipient. Also disclosed is a use of the 2-(2,4,5-substituted aniline) pyrimidine derivative, a solvate, or a pharmaceutically acceptable salt thereof in the preparation of drugs for treating cancers. The compounds of the present invention have a relatively high solubility in water and a relatively high permeability, and/or a relatively low binding ability to plasma proteins, and at the same time have a relatively low toxicity characteristic and a relatively high anti-tumor activity.

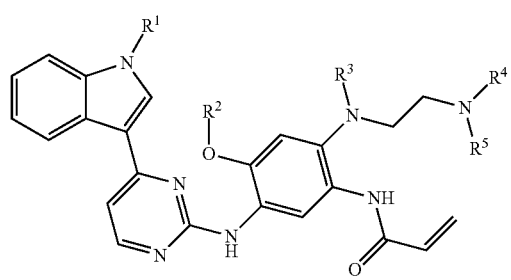

4 Claims, 2 Drawing Sheets

(56) References Cited

OTHER PUBLICATIONS

Advances in drug research, vol. 14. Edited by Bernard Testa.
Apr. 16, 2018 Office Action issued in related Korean application No. 10-2017-7007190.

* cited by examiner

2-(2,4,5-SUBSTITUTED ANILINE) PYRIMIDINE DERIVATIVE, PHARMACEUTICAL COMPOSITION AND USE THEREOF

This application claims priority from CN application No. CN 201410401604.7, filed on Aug. 15, 2014. The entire contents of the above-mentioned application are incorporated herein by reference.

FIELD OF INVENTION

The present invention relates to a 2-(2,4,5-substituted aniline)pyrimidine derivative, a pharmaceutical composition and a use thereof.

PRIOR ARTS

EGFR is a transmembrane protein tyrosine kinase member of the erbB receptor family. When binding with the growth factor ligands (e.g., the epidermal growth factor (EGF)), EGFR can homo-dimerize with the additional EGFR molecule, or hetero-dimerize with another family member (such as erbB2 (HER2), erbB3 (HER3), or erbB4 (HER4)).

Dysregulation of the erbB family signaling promotes proliferation, invasion, metastasis, angiogenesis, and tumor cell survival, and which has been described in many human cancers (including lung cancer, head and neck cancer and breast cancer). Thus, the erbB family represents a reasonable target for the anticancer drugs' development, many medicaments targeting EGFR or erbB2 are now available in clinical, including gefitinib, erlotinib, lapatinib.

It was reported in 2004 (Science [2004] Issue 304, 1497-500 and New England Journal of medicine [2004] Issue 350, 2129-39) that the activation of EGFR mutations is related to the response to the treatment of gefitinib against non-small cell lung cancer (NSCLC). The most common EGFR mutations (L858R and delE746_A750) result in an increase of affinity to small molecule tyrosine kinase inhibitors (e.g. gefitinib and erlotinib), and a decrease of the affinity to adenosine triphosphate (ATP), relative to wild type (WT) EGFR. Finally, the acquired resistance to the treatment of gefitinib or erlotinib occurs, such as, due to the mutation of the gatekeeper residue T790M, according to reports, the mutation was found in 50% of clinical drug resistance patients. The mutation was not considered to block the combination of gefitinib or erlotinib with EGFR in space, only modulate the affinity to ATP to a level equivalent to WTEGFR.

In view of the importance of this mutation in the resistance to existing therapies targeting EGFR, it is believed that drugs targeting EGFR which can inhibit the mutation of the gene, including the gatekeeper gene, are particularly useful in the treatment of cancer. Compared with the activated mutation forms of EGFR (such as the L858R EGFR mutant or the delE746 A750 mutant, or the Exon19 deletion EGFR mutant) and/or the resistant mutation forms of EGFR (such as T790M EGFR mutant), compounds with selectivity which can exhibit favorable performance on WT EGFR and/or other enzyme receptors are still required, the selectivity of these compounds makes them have a promising prospect in being developed into therapeutic agents.

CN application CN 201280033773 discloses compound AZD9291 represented by formula (II), which is effective in treating T790M EGFR mutant tumors, but it is easily metabolized due to demethylation in vivo, and this increases the burden of liver metabolism, thereby resulting in hepatotoxicity. The product of the metabolism increases the toxicity and causes shorter half-life in vivo, and ultimately affects the anti-cancer activity of the drug.

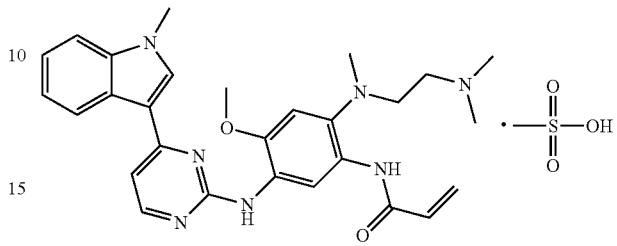

Formula (II)

Content of the Present Invention

The technical problem to be solved by the present invention is that in order to cure the defects of an unsatisfactory inhibitory activity and high toxicity of EGFR/EGFR mutant inhibitor in the prior art, it provides a novel 2-(2,4,5-substituted aniline) pyrimidine derivative, a pharmaceutical composition and a use thereof. The 2-(2,4,5-substituted aniline) pyrimidine derivatives in the present invention have higher water solubility, higher permeability, and/or lower plasma protein binding capacity, as well as lower toxicity and higher antitumor activity.

The present invention provides a 2-(2,4,5-substituted aniline) pyrimidine derivative represented by formula I, or a solvate, or a pharmaceutically acceptable salt thereof,

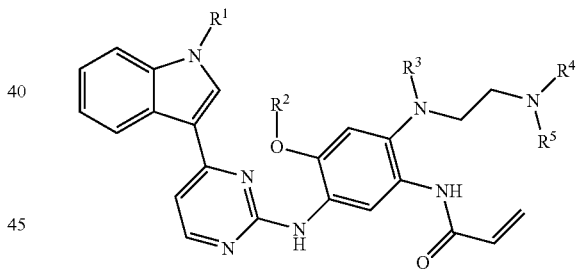

Formula (I)

wherein:

$R^1$ represents a methyl or a methyl substituted by 1 to 3 of deuterium atom(s);

$R^2$ represents a methyl or a methyl substituted by 1 to 3 of deuterium atom(s);

$R^3$ represents a methyl or a methyl substituted by 1 to 3 of deuterium atom(s);

$R^4$ represents a methyl or a methyl substituted by 1 to 3 of deuterium atom(s);

$R^5$ represents a methyl or a methyl substituted by 1 to 3 of deuterium atom(s);

provided that at least one of $R^1$, $R^2$, $R^3$, $R^4$ and $R^5$ represents a methyl substituted by 1 to 3 of deuterium atoms.

The methyl substituted by 1 to 3 of deuterium atoms is preferably a tri-deuterated methyl.

The 2-(2,4,5-substituted aniline) pyrimidine derivative represented by formula I, or the solvate, or the pharmaceutically acceptable salt thereof, is preferably selected from the group consisting of N-(2-{2-dimethylaminoethyl-methylamino}-4-methoxy-5-{[4-(1-(D₃-methyl)indol-3-yl)pyrimidin-2-yl]amino}phenyl)-2-acrylamide;

N-(2-{2-dimethylaminoethyl-methylamino}-4-(D₃-methoxy)-5-{[4-(1-methylindol-3-yl)pyrimidin-2-yl]amino}phenyl)-2-acrylamide;

N-(2-{2-dimethylaminoethyl-(D₃-methyl)amino}-4-methoxy-5-{[4-(1-methylindol-3-yl)pyrimidin-2-yl]amino}phenyl)-2-acrylamide;

N-(2-{2-di(D₃-methyl)aminoethyl-methylamino}-4-methoxy-5-{[4-(1-methylindol-3-yl)pyrimidin-2-yl]amino}phenyl)-2-acrylamide;

N-(2-{2-[methyl(D₃-methyl)amino]ethyl-methylamino}-4-methoxy-5-{[4-(1-methylindol-3-yl)pyrimidin-2-yl]amino}phenyl)-2-acrylamide;

N-(2-{2-di(D₃-methyl)aminoethyl-methylamino}-4-methoxy-5-{[4-(1-(D₃-methyl)indol-3-yl)pyrimidin-2-yl]amino}phenyl)-2-acrylamide.

The 2-(2,4,5-substituted aniline)pyrimidine derivative represented by formula I, or the solvate, or the pharmaceutically acceptable salt thereof, wherein the pharmaceutically acceptable salt includes a salt of inorganic acid and a salt of organic acid. The salt of inorganic acid is typically hydrochloride, hydrobromide, hydriodate, sulfate, phosphate, carbonate, a salt of hydrogen disulfide etc. The salt of organic acid is typically p-toluene sulfonate, salicylate, tartrate, hydrogen tartrate, ascorbate, maleate, benzene sulfonate, fumarate, gluconate, glucuronate, formate, glutamate, mesylate, esylate, benzene sulfonate, lactate, oxalate, brosylate, citrate, benzoate, malate, acetate etc., preferably mesylate.

The present invention further provides a pharmaceutical composition, which comprises a therapeutically effective amount of the 2-(2,4,5-substituted aniline)pyrimidine derivative represented by formula I, or the solvate, or the pharmaceutically acceptable salt thereof, and a pharmaceutically acceptable excipient.

In the present invention, the pharmaceutical composition can be prepared into various unit administrations, such as tablet, pill, powder, liquid, suspension, emulsion, granule, capsule, suppository and injection (solution and suspension) etc., preferably liquid, suspension, emulsion, suppository and injection (solution and suspension) etc.

Any excipient which is well known and widely used in the art can be employed to prepare tablets of the pharmaceutical composition. For example, a carrier, such as lactose, sugar, sodium chloride, glucose, urea, starch, calcium carbonate, kaolin, crystalline cellulose and silicic acid, etc.; an adhesive, such as water, ethanol, propanol, common syrup, glucose solution, starch solution, gelatin solution, carboxymethylcellulose, lakn, methylcellulose and potassium phosphate, polyvinylpyrrolidone etc.; a disintegrant, such as dry starch, sodium alginate, agar powder and kelp powder, sodium bicarbonate, calcium carbonate, polyethylene sorbitan aliphatic acid ester, lauryl sodium sulfate, glycerol monostearate, starch and lactose etc.; a disintegration inhibitor, such as sugar, glycerol tristearate, coconut oil and hydrogenated oil; an adsorbed accelerator, such as quaternary ammonium salt and lauryl sodium sulfate etc.; a moistening agent, such as glycerol, starch etc.; an adsorbent, such as starch, lactose, kaolin, bentonite and colloidal silica etc.; as well as a lubricant such as pure talc, stearate, boric acid powder and polyethylene glycol etc. Also, if desired, an ordinary coating material can be employed to prepare sugar coated tablet, gelatin coated tablet, enteric coated tablet, coated tablet, bilayer tablet and multilayer tablet.

Any excipient which is well known and widely used in the art can be employed to prepare pills of the pharmaceutical composition. For example, a carrier, such as lactose, starch, coconut oil, vegetable oil, kaolin and talc etc.; an adhesive, such as arabia gum, tragacanth powder, gelatin and ethanol etc.; a disintegrant, such as agar and kelp powder etc.

Any excipient which is well known and widely used in the art can be employed to prepare suppositories of the pharmaceutical composition. For example, polyethylene glycol, coconut oil, higher alcohol, ester of higher alcohol, glutin and semi synthetic glyceride etc.

The sterilized solution or suspension (preferably adding proper amount of sodium chloride, glucose, or glycerin, etc.) can be made into an injection isotonic with blood pressure thereby forming an injection of the pharmaceutical composition. Any carrier commonly used in the art can be employed to prepare injection formulation. For example, water, ethanol, propylene glycol, ethoxylated stearyl alcohol, polyoxylated stearyl alcohol, and polyethylene sorbitan aliphatic acid ester etc. Additionally, an ordinary solubilizer, buffer, analgesic agent and the like can also be added.

In the present invention, there are no special requirements to the amount of active ingredient contained in the pharmaceutical composition, which can adapt a wide range scope, and commonly can be 10 to 90% (wt %), preferably 30 to 80% (wt %).

In the present invention, there are no special requirements to the administration of the pharmaceutical composition. Formulations can be administered depending on the patient's age, gender and other conditions and symptoms. For example, tablet, pill, liquid, suspension, emulsion, granule or capsule for oral administration; an injection can be administrated separately, or mixed with an injection fluid (such as glucose solution and mino acid solution) for intravenous injection; a suppository was administrated to the rectum.

The pharmaceutical composition may also contain other pharmaceutical active ingredients, which are administrated in combination with the 2-(2,4,5-substituted aniline)pyrimidine derivative represented by formula I, or the solvate, or the pharmaceutically acceptable salt thereof. The other pharmaceutical active ingredients can be known medicinal active ingredients with anticancer effect, such as 5-fluorouracil, cisplatin, oxaliplatin, gefitinib, erlotinib, pazopanib, afatinib, cetuximab or bevacizumab etc.

The present invention further provides a use of the 2-(2,4,5-substituted aniline)pyrimidine derivative represented by formula I, or the solvate, or the pharmaceutically acceptable salt thereof or the pharmaceutical composition in manufacturing a drug for the treatment of cancers.

The cancer can be selected from the group consisting of ovarian cancer, cervical cancer, colorectal cancer, breast cancer, bladder cancer, brain tumor, pancreatic cancer, astrocytoma, liver cancer, glioma, glioblastoma, prostate cancer, thymic carcinoma, leukemia, lymphoma, non Hodgkin lymphoma, gastric cancer, lung cancer, liver cell cancer, gastrointestinal stromal tumor (GIST), thyroid carcinoma, medullary thyroid carcinoma, glioma, neuroblastoma, bile duct cancer, endometrial cancer, kidney tumor, kidney cancer, head and neck cancer, anaplastic large cell lymphoma, acute myeloid leukemia (AML), multiple myeloma, melanoma, mesothelioma; preferably lung cancer, more preferably non small-cell lung cancer.

DETAILED DESCRIPTION OF THE PREFERRED EMBODIMENT

Embodiment 1A

Figure 1:
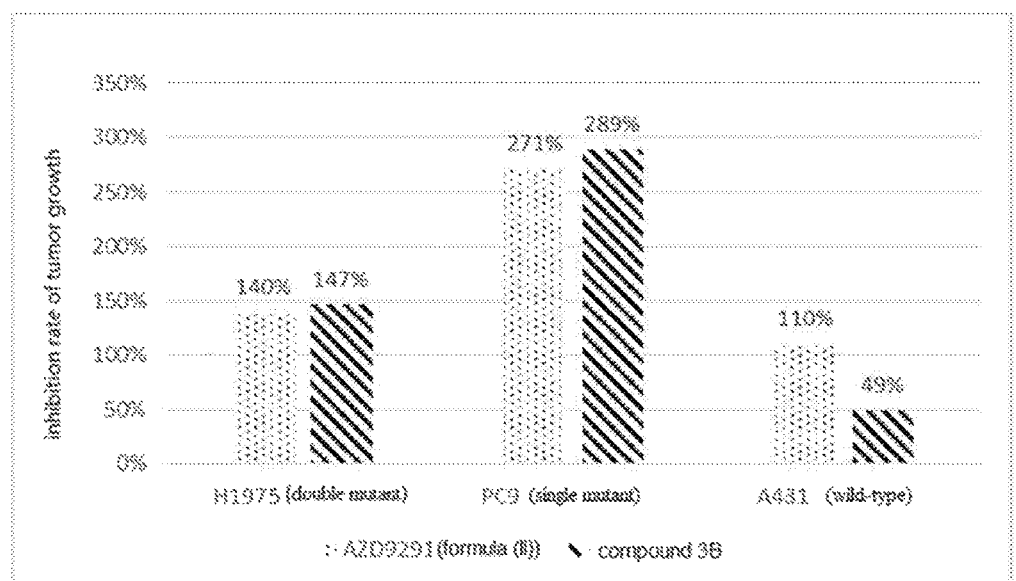
FIG. 1 is the result of tumor growth inhibitory test for the tumor-bearing nude mice administered with compound 3B and AZD9291 at a dose of 10 mg/kg/Day over 10 days.

N-(2-{2-[methyl($D_3$-methyl)amino]ethyl-methyl-amino}-4-methoxy-5-{[4-(1-methylindol-3-yl)pyrimidin-2-yl]amino}phenyl)-2-acrylamide

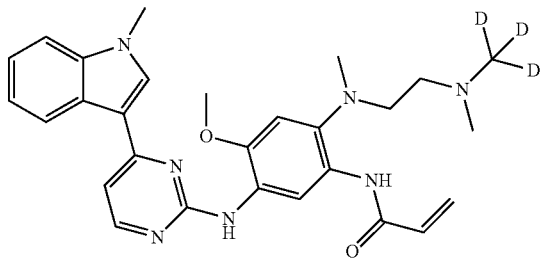 [SMILES: [2H]C([2H])([2H])N(C)CCN(C)c1cc(OC)c(Nc2nccc(-c3cn(C)c4ccccc34)n2)cc1NC(=O)C=C]

Under ice bath condition, to $N^1$-(2-[methyl($D_3$-methyl)amino]ethyl)-5-methoxy-$N^1$-methyl-$N^4$-[4-(1-methylindol-3-yl)pyrimidin-2-yl]phenyl-1,2,4-triamine (intermediate 1, 20 g) in THF (200 mL) and water (20 mL), was added 6.9 g NaOH. Acryloyl chloride 4.05 g was added while stirring, the reaction mixture was stirred for 30 min at room temperature, then stirred for 1 h at room temperature. After the result of TLC showed that the reaction was complete, 200 mL water and 20 mL aqueous ammonia were added into the reaction mixture, the solid was precipitated and filtered out. The solid was collected and washed with water, dried for 8 h at 50° C. to deliver the title compound (yield 86%).

$^1$H-NMR: 2.70 (3H, s), 2.84 (3H, s), 3.37 (4H, s), 3.86 (3H, s), 3.92 (3H, s), 5.76 (1H, d), 6.28 (1H, d), 6.66 (1H, dd), 7.04-7.25 (2H, m), 7.29 (1H, t), 7.44 (1H, d), 7.59 (1H, d), 8.25 (2H, s), 8.83 (1H, s), 9.45 (1H, s), 9.54 (1H, s).

ESI+: [M+H$^+$] 503.29

Embodiment 1B

N-(2-{2-[methyl($D_3$-methyl)amino]ethyl-methyl-amino}-4-methoxy-5-{[4-(1-methylindol-3-yl)pyrimidin-2-yl]amino}phenyl)-2-acrylamide mesylate Into a 500 mL three-neck flask, was added N-(2-{2-[methyl($D_3$-methyl)amino]ethyl-methylamino}-4-methoxy-5-{[4-(1-methylindol-3-yl)pyrimidin-2-yl]amino}phenyl)-2-acrylamide 20.5 g (1.0 eq) obtained according to embodiment 1A, and dissolved in 120 mL ethanol and 80 mL ethyl acetate, 4.1 g methylsulfonic acid (1.05 eq) and 40 mL ethyl acetate were added dropwise at room temperature within about 1 h. After addition, the temperature was kept for 1.5 to 2 h, then cooled to room temperature slowly. The reaction mixture was filtered and the filter cake was washed by ethyl acetate/ethanol (2:1, v/v) once, filtered out and dried to deliver 18.0 g product, yield 83%.

Embodiment 2A

N-(2-{2-di($D_3$-methyl)aminoethyl-methylamino}-4-methoxy-5-{[4-(1-methylin dol-3-yl)pyrimidin-2-yl]amino}phenyl)-2-acrylamide

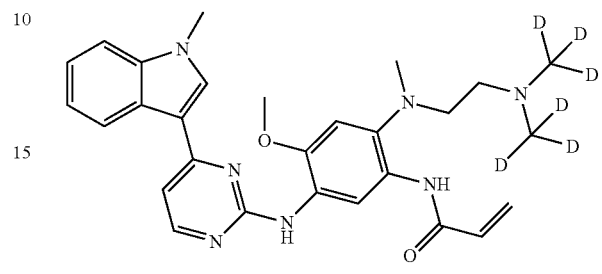

Under ice bath condition, to $N^1$-(2-[di($D_3$-methyl)amino]ethyl)-5-methoxy-$N^1$-methyl-$N^4$-[4-(1-methylindol-3-yl)pyrimidin-2-yl]phenyl-1,2,4-triamine (intermediate 2, 20 g) in THF (200 mL) and water (20 mL), was added 6.9 g NaOH. Acryloyl chloride 4.05 g was added while stirring, the reaction mixture was stirred for 30 min at room temperature, then stirred for 1 h at room temperature. After the result of TLC showed that the reaction was complete, 200 mL water and 20 mL aqueous ammonia were added into the reaction mixture, the solid was precipitated and filtered out. The solid was collected and washed with water, dried for 8 h at 50° C. to deliver the title compound (yield 88%).

$^1$H-NMR: 2.72 (3H, s), 3.35 (4H, s), 3.88 (3H, s), 3.921 (3H, s), 5.78 (1H, d), 6.26 (1H, d), 6.67 (1H, dd), 7.04-7.24 (2H, m), 7.30 (1H, t), 7.43 (1H, d), 7.58 (1H, d), 8.24 (2H, s), 8.84 (1H, s), 9.44 (1H, s), 9.55 (1H, s).

ESI+: [M+H$^+$] 506.30.

Embodiment 2B

N-(2-{2-di($D_3$-methyl)aminoethyl-methylamino}-4-methoxy-5-{[4-(1-methylin dol-3-yl)pyrimidin-2-yl]amino}phenyl)-2-acrylamide mesylate Into a 500 mL three-neck flask, was added N-(2-{2-di($D_3$-methyl)aminoethyl-methylamino}-4-methoxy-5-{[4-(1-methylindol-3-yl)pyrimidin-2-yl]amino}phenyl)-2-acrylamide 20.5 g (1.0 eq) obtained according to embodiment 2A, and dissolved in 120 mL ethanol and 80 mL ethyl acetate, 4.1 g methylsulfonic acid (1.05 eq) and 40 mL ethyl acetate were added dropwise at room temperature within around 1 h. After addition, the temperature was kept for 1.5 to 2 hrs, and then cooled to room temperature slowly. The reaction mixture was filtered and the filter cake was washed by ethyl acetate/ethanol (2:1, v/v) once, filtered out and dried to deliver a yellow solid, yield 85%.

Embodiment 3A

N-(2-{2-dimethylaminoethyl-methylamino}-4-methoxy-5-{[4-(1-(D$_3$-methyl)indol-3-yl)pyrimidin-2-yl]amino}phenyl)-2-acrylamide

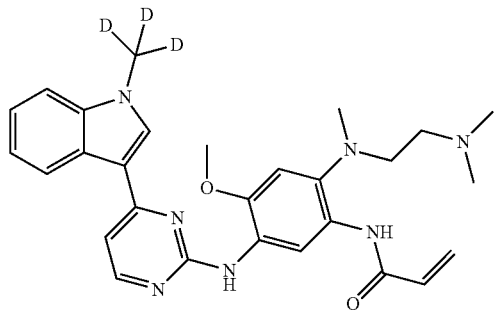 [SMILES: [2H]C([2H])([2H])n1cc(-c2ccnc(Nc3cc(NC(=O)C=C)c(N(C)CCN(C)C)cc3OC)n2)c2ccccc21]

Under ice bath condition, to N$^1$-(2-dimethylaminoethyl)-5-methoxy-N$^1$-methyl-N$^4$-[4-(1-[D$_3$-methylindol]-3-yl)pyrimidin-2-yl]phenyl-1,2,4-triamine (intermediate 3, 20 g) in THF (200 mL) and water (20 mL), was added 6.9 g NaOH. Acryloyl chloride 4.05 g was added while stirring, the reaction mixture was stirred for 30 min at room temperature, then stirred for 1 h at room temperature. After the result of TLC showed that the reaction was complete, 200 mL water and 20 mL aqueous ammonia were added into the reaction mixture, the solid was precipitated and filtered out. The solid was collected and washed with water, dried for 8 h at 50° C. to deliver the title compound (yield 87%).

$^1$H-NMR: 2.70 (3H, s), 2.88 (6H, d), 3.35 (4H, s), 3.92 (3H, s), 5.77 (1H, d), 6.27 (1H, d), 6.67 (1H, dd), 7.04-7.25 (2H, m), 7.28 (1H, t), 7.46 (1H, d), 7.59 (1H, d), 8.23 (2H, s), 8.85 (1H, s), 9.45 (1H, s), 9.55 (1H, s).

ESI+: [M+H$^+$] 503.29.

Embodiment 3B

N-(2-{2-dimethylaminoethyl-methylamino}-4-methoxy-5-{[4-(1-D$_3$-methyl)indol-3-yl)pyrimidin-2-yl]amino}phenyl)-2-acrylamide mesylate Into a 500 mL three-neck flask, was added N-(2-{2-dimethylaminoethyl-methylamino}-4-methoxy-5-{[4-(1-(D$_3$-methyl)indol-3-yl)pyrimidin-2-yl]amino}phenyl)-2-acrylamide 20.5 g (1.0 eq) obtained according to embodiment 3A, and dissolved in 120 mL ethanol and 80 mL ethyl acetate, 4.1 g methylsulfonic acid (1.05 eq) and 40 mL ethyl acetate were added dropwise at room temperature within about 1 h. After the addition, the temperature was kept for 1.5 to 2 hrs, and then cooled to room temperature slowly. The reaction mixture was filtered and the filter cake was washed by ethyl acetate/ethanol solution (2:1, v/v) once, filtered out and dried to deliver a yellow solid, yield 81%.

Embodiment 4A

N-(2-{2-dimethylaminoethyl-methylamino}-4-(D$_3$-methoxy)-5-{[4-(1-methylindol-3-yl)pyrimidin-2-yl]amino}phenyl)-2-acrylamide

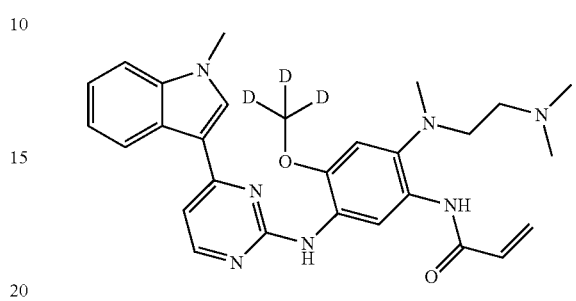

Under ice bath condition, to N$^1$-(2-dimethylaminoethyl)-5-(D$_3$-methoxy)-N$^1$-methyl-N$^4$-[4-(1-methylindol)-3-yl)pyrimidin-2-yl]phenyl-1,2,4-triamine (intermediate 4, 20 g) in THF (200 mL) and water (20 mL), was added 6.9 g NaOH. Acryloyl chloride 4.05 g was added while stirring, the reaction mixture was stirred for 30 min at room temperature, then stirred for 1 h at room temperature. After the result of TLC showed that reaction was complete, 200 mL water and 20 mL aqueous ammonia were added into the reaction mixture, the solid was precipitated and filtered out. The solid was collected and washed with water, dried for 8 h at 50° C. to deliver the title compound (yield 85%).

$^1$H-NMR: 2.70 (3H, s), 2.88 (6H, d), 3.35 (4H, s), 3.86 (3H, s), 5.77 (1H, d), 6.27 (1H, d), 6.67 (1H, dd), 7.04-7.25 (2H, m), 7.28 (1H, t), 7.46 (1H, d), 7.59 (1H, d), 8.23 (2H, s), 8.85 (1H, s), 9.45 (1H, s), 9.55 (1H, s).

ESI+: [M+H$^+$] 503.29.

Embodiment 4B

N-(2-{2-dimethylaminoethyl-methylamino}-4-(D$_3$-methoxy)-5-{[4-(1-methylindol-3-yl)pyrimidin-2-yl]amino}phenyl)-2-acrylamide mesylate Into a 500 mL three-neck flask, was added N-(2-{2-dimethylaminoethyl-methylamino}-4-(D$_3$-methoxy)-5-{[4-(1-methylindol-3-yl)pyrimidin-2-yl]amino}phenyl)-2-acrylamide 20.5 g (1.0 eq) obtained according to embodiment 4A, and dissolved in 120 mL ethanol and 80 mL ethyl acetate, 4.1 g methylsulfonic acid (1.05 eq) and 40 mL ethyl acetate were added dropwise at room temperature within about 1 h. After the addition, the temperature was kept for 1.5 to 2 hrs, then cooled to room temperature slowly. The reaction mixture was filtered and the filter cake was washed by ethyl acetate/ethanol solution (2:1, v/v) once, filtered out and dried to deliver a yellow solid, yield 88%.

Embodiment 5A

N-(2-{2-dimethylaminoethyl-(D$_3$-methyl)amino}-4-methoxy-5-{[4-(1-methylindol-3-yl)pyrimidin-2-yl]amino}phenyl)-2-acrylamide

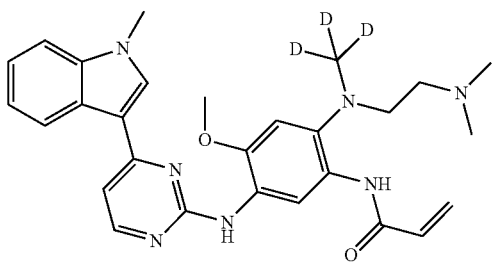 [SMILES: [2H]C([2H])([2H])N(CCN(C)C)c1cc(OC)c(Nc2nccc(-c3cn(C)c4ccccc34)n2)cc1NC(=O)C=C]

The process is the same as N-(2-{2-dimethylaminoethyl-methylamino}-4-(D$_3$-methoxy)-5-{[4-(1-methylindol-3-yl)pyrimidin-2-yl]amino}phenyl)-2-acrylamide, except for that the reactant is N$^1$-(2-dimethylaminoethyl)-5-methoxy-N$^1$-(D$_3$-methyl)-N$^4$-[4-(1-methylindol-3-yl)pyrimidin-2-yl]benzene-1,2,4-triamine, and the yield is 70%.

ESI+: [M+H$^+$] 503.29.

Embodiment 5B

N-(2-{2-dimethylaminoethyl-(D$_3$-methyl)amino}-4-methoxy-5-{[4-(1-methylindol-3-yl)pyrimidin-2-yl]amino}phenyl)-2-acrylamide mesylate The process is the same as N-(2-{2-dimethylaminoethyl-methylamino}-4-(D$_3$-methoxy)-5-{[4-(1-methylindol-3-yl)pyrimidin-2-yl]amino}phenyl)-2-acrylamide mesylate, except for that the reactant is N-(2-{2-dimethylaminoethyl-(D$_3$-methyl)amino}-4-methoxy-5-{[4-(1-methylindol-3-yl)pyrimidin-2-yl]amino}phenyl)-2-acrylamide obtained according to embodiment 5A, yellow solid, yield 79%.

Embodiment 6A

N-(2-{2-di(D$_3$-methyl)aminoethyl-methylamino}-4-methoxy-5-{[4-(1-(D$_3$-methyl)indol-3-yl)pyrimidin-2-yl]amino}phenyl)-2-acrylamide

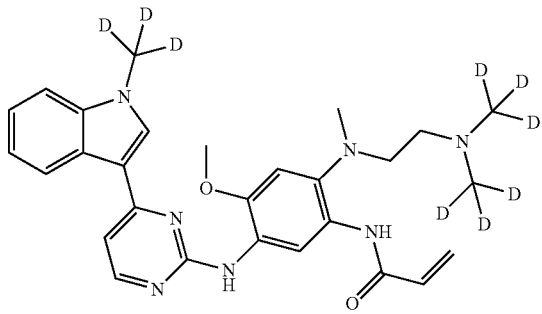 [SMILES: [2H]C([2H])([2H])N(CCN(C)c1cc(OC)c(Nc2nccc(-c3cn(C([2H])([2H])[2H])c4ccccc34)n2)cc1NC(=O)C=C)C([2H])([2H])[2H]]

The process is the same as compound 2A N-(2-{2-di(D$_3$-methyl)aminoethyl-methylamino}-4-methoxy-5-{[4-(1-methylindol-3-yl)pyrimidin-2-yl]amino}phenyl)-2-acrylamide, except for that the reactant is N$^1$-(2-di(D$_3$-methyl)amino-ethyl)-5-methoxy-N$^1$-methyl-N$^4$-[4-(1-[D$_3$-methylindol]-3-yl)pyrimidin-2-yl]benzene-1,2,4-triamine.

ESI+: [M+H$^+$] 509.34

Embodiment 6B

N-(2-{2-di(D$_3$-methyl)aminoethyl-methylamino}-4-methoxy-5-{[4-(1-(D$_3$-methyl)indol-3-yl)pyrimidin-2-yl]amino}phenyl)-2-acrylamide mesylate The process is the same as N-(2-{2-dimethylaminoethyl-methylamino}-4-(D$_3$-methoxy)-5-{[4-(1-methylindol-3-yl)pyrimidin-2-yl]amino}phenyl)-2-acrylamide mesylate, except for that the reactant is N-(2-{2-di(D$_3$-methyl)amino-ethyl-methylamino}-4-methoxy-5-{[4-(1-(D$_3$-methyl)indol-3-yl)pyrimidin-2-yl]amino}phenyl)-2-acrylamide obtained according to embodiment 6A, yellow solid, yield 59%.

Embodiment 7

Intermediate 1: N$^1$-(2-[methyl(D$_3$-methyl)amino]ethyl)-5-methoxy-N$^1$-methyl-N$^4$-[4-(1-methylindol-3-yl)pyrimidin-2-yl]benzene-1,2,4-triamine (intermediate 1)

A mixture of N$^1$-(2-[methyl(D$_3$-methyl)amino]ethyl)-2-methoxy-N$^1$-methyl-N-[4-(1-methylindol-3-yl)pyrimidin-2-yl]-5-nitrobenzene-1,4-diamine (44 g), iron (31 g) and NH$_4$Cl (1.9 g) in ethanol (120 mL) and water (40 mL) was heated to reflux for 3.5 h. The crude mixture was purified by ion exchange chromatography with SCX column, eluted with methanol-ammonia, concentrated under vacuum to give a beige title compound (90%).

Intermediate 2: N$^1$-(2-[di(D$_3$-methyl)amino]ethyl)-5-methoxy-N$^1$-methyl-N$^4$-[4-(1-methylindol-3-yl)pyrimidin-2-yl]benzene-1,2,4-triamine Intermediate 3: N$^1$-(2-dimethylaminoethyl)-5-methoxy-N$^1$-methyl-N$^4$-[4-(1-[D$_3$-methylindol]-3-yl)pyrimidin-2-yl]benzene-1,2,4-triamine The process for preparing intermediate 3 referred to the process for preparing intermediate 1: reacting intermediate 8 with 2,4-dichloropyrimidine to afford 3-(2-chloropyrimidin-4-yl)-1-(D$_3$-methyl)indole, and then reacting the obtained product with 4-fluoro-2-methoxy-5-nitroaniline to afford N-(4-fluoro-2-methoxy-5-nitrophenyl)-4-([1-D$_3$-methylindol]-3-yl)pyrimidin-2-amine at the presence of p-methylbenzenesulfonic acid, the product was then reacted with N,N'-dimethyl-N'-methylethane at the presence of DIPEA to afford N'-(2-[dimethylamino]ethyl)-2-methoxy-N'-methyl-N-[4-([D$_3$-methylindol]-3-yl)pyrimidin-2-yl]-5-nitrobenzene-1,4-diamine, which was reduced by iron and NH$_4$Cl to afford intermediate 3.

Intermediate 4: N$^1$-(2-dimethylaminoethyl)-5-(D$_3$-methoxy)-N$^1$-methyl-N$^4$-[4-(1-methylindol)-3-yl)pyrimidin-2-yl]benzene-1,2,4-triamine The process for preparing intermediate 2 to 4 was the same as that for intermediate 1, except for that the reactant is the corresponding reactants of each intermediates, the reactant for intermediate 2 is N'-([di(D$_3$-methyl)amino]ethyl)-2-methoxy-N'-methyl-N-[4-(1-methylindol-3-yl)pyrimidin-2-yl]-5-nitrophenyl-1,4-diamine, the reactant for intermediate 3 is 1\142-[dim ethyl amino]ethyl)-2-methoxy-N'-methyl-N-[4-(1-[D$_3$-methylindol]-3-yl)pyrimidin-2-yl]-5-nitrobenzene-1,4-diamine, the reactant for intermediate 4 is N'-(dimethylaminoethyl)-2-(D$_3$-methoxy)-N'-methyl-N-[4-(1-methylindol-3-yl)pyrimidin-2-yl]-5-nitrobenzene-1,4-diamine.

Intermediate 5: N'-(2-dimethylaminoethyl)-2-methoxy-N'-(D$_3$-methyl)-N-[4-(1-methylindol-3-yl)pyrimidin-2-yl]-5-nitrobenzene-1,4-diamine To a 500 mL three-neck flask, were added 190 mL DMA, 16.9 g N,N'-dimethyl-N'-(D$_3$-methyl)-ethane, 23.1 g DIPEA, stirred for 30 min at room temperature, 47 N-(4-fluoro-2-methoxy-5-nitrophenyl)-4-(1-methylindol-3-yl)pyrimidin-2-amine (intermediate 6) was added, the resultant solid-liquid suspension was then heated to 85° C. and reacted for 2 to 3 h. After the results of TLC and MS showed that the reaction was complete, filtered while the mixture was hot. 300 mL acetonitrile was added into the filtrate, the mixture was cooled to about 5° C. and large amount of red product was precipitated, filtered out, dried under reduced pressure at 50° C. to deliver 51 g product, yield 90%, which was used directly in the next step without purification.

Intermediate 6: N-(4-fluoro-2-methoxy-5-nitrophenyl)-4-(1-methylindol-3-yl)pyrimidin-2-amine To a 1 L three-neck flask equipped with mechanical agitation, were added 500 mL 1,4-dioxane and 30 g 3-(2-chloropyrimidin-4-yl)-1-methylindole (intermediate 7), 30 g p-toluenesulfonic acid and 46 g 4-fluoro-2-methoxy-5-nitroaniline were added while stirring, then the resultant solid-liquid suspension was heated to 95 to 102° C. and reacted for 3 h. After the result of TLC showed that the reaction was complete, the mixture was cooled to 60° C., diluted conc. aqueous ammonia was added dropwise, pH was adjusted, then cooled to 10 to 15° C. and stirred for 30 min, filtered, the filter cake was washed with 5% NaHCO$_3$ solution once, then cold ethanol once, filtered out and dried at 50° C. to deliver 47 g product, yield 74%, which was used directly in the next step without purification.

Intermediate 7: 3-(2-chloropyrimidin-4-yl)-1-methylindole

To a 1 L three-neck flask, were added 40 g 2,4-dichloropyrimidine and 200 mL DME, after dissolved, cooled to 10 to 15° C., 45 g anhydrous FeCl$_3$ was added in portions rapidly, the temperature was kept at or below 35° C., and the mixture was stirred for 15 min after each portion was added. 52.8 g 1-methylindole was added dropwise into the above reaction system, then the mixture was heated slowly to 50° C., stirred overnight, the reaction was monitored by TLC until it finished. The reaction mixture was cooled to 5 to 10° C., about 300 mL methanol aqueous solution (1:2, v/v) was slowly added dropwise and large amount of viscous solid was precipitated. The mixture was filtered, the filter cake was washed with methanol twice, after filtration, dried under reduced pressure at 50° C., yield 85%.

Intermediate 8: 1-(D$_3$-methyl)indole 5 g indole was dissolved in 20 mL DCM, 0.5 g K$_2$CO$_3$ was added, 2 mL deuterated iodomethane in DCM was added dropwise under ice bath condition, the mixture was reacted at room temperature for 3 h, the result of TLC showed that the reaction was complete. A solution of sodium sulfite was added, and the mixture was extracted and concentrated by rotatory evaporator to deliver the product, yield 95%.

Effect Embodiment 1

According to the method described in R&D Systems DuoSet IC Human Phospho-EGF R ELISA (R&D Systems Cat. No. #DYC1095), assay was performed to measure the intracellular phosphorylation of endogenous p-EGFR in the cell lysate. The contents of the reference were incorporated herein by its entirety.

Test 1: Assay on Intracellular Phosphorylation of Exon19 Deletion EGFR (Activated Single Mutant).

The human lung cell line PC9 (Exon19 deletion EGFR) (purchased from China Pharmaceutical University) was kept in the RPMI1640 containing 10% fetal bovine serum and 2 mM glutamine. Cells were incubated at 37° C. in the humidifying incubator with 5% CO$_2$. 40 μL Cells were seeded (10000 cells/well) in medium contained in a 384-well Corning black transparent bottom plate, and incubated overnight at 37° C. under 5% CO$_2$. Acoustically dosed with Echo555, the continuously diluted compound which was to be tested in 100% DMSO was added to the cells. After the cells were incubated for 2 h, mixed with the medium gently, 40 μL lysis buffer was added to each well. The 384-well high cohesion black Greiner plate were covered with capture antibody, and then blocked with 3% BSA. Then the blocking liquid was removed, 15 μL lysis buffer was transferred to 384-well high cohesion black Greiner plate, incubated for 2 h, gently mixed and washed with PBS, 20 μL antibody was added, incubated for 2 h, gently mixed and washed with PBS, 20 μL QuantaBlu fluorescent peroxidase substrate (Thermo Fisher Scientific) was added and incubated for 1 h. 20 μL terminating solution of QuantaBlu was added to the plate, and the fluorescence was read by Envision microplate detector which employed an excitation wavelength of 352 nm and an emission wavelength of 460 nm. The obtained data of the compounds to be tested were input into the appropriate software package to perform curve fitting analysis. IC$_{50}$ value was determined by calculating the concentration of the compound when 50% effect was acquired based on these data.

Test 2: Assay on Intracellular Phosphorylation of L858R/T790M EGFR (Double Mutant)

The human lung cell line NCI-H1975 (purchased from China Pharmaceutical University) was kept in the RPMI1640 containing 10% fetal bovine serum and 2 mM glutamine. Cells were incubated at 37° C. in the humidifying incubator with 5% CO$_2$. 40 μL Cells were seeded (10000 cells/well) in medium contained in a 384-well Corning black transparent bottom plate, and incubated overnight at 37° C. under 5% CO$_2$. Acoustically dosed with Echo555, the continuously diluted compound which was to be tested in 100% DMSO was added to the cells. After the cells were incubated for 2 h, mixed with the medium gently, 40 μL lysis buffer was added to each well. The 384-well high cohesion black Greiner plate were covered with capture antibody, and then blocked with 3% BSA. Then the blocking liquid was removed, 15 μL lysis buffer was transferred to 384-well high cohesion black Greiner plate, incubated for 2 h, gently mixed and washed with PBS, 20 μL antibody was added, incubated for 2 h, gently mixed and washed with PBS, 20 μL QuantaBlu fluorescent peroxidase substrate (Thermo Fisher Scientific) was added and incubated for 1 h. 20 μL terminating solution of QuantaBlu was added to the plate, and the fluorescence was read by Envision microplate detector which employed an excitation wavelength of 352 nm and an emission wavelength of 460 nm. The obtained data of the compounds to be tested were input into the appropriate software package to perform curve fitting analysis. $IC_{50}$ value was determined by calculating the concentration of the compound when 50% effect was acquired based on these data.

Test 3: Assay on Intracellular Phosphorylation of Wild-Type EGFR

The human colon cell line LoVo (purchased from China Pharmaceutical University) was kept in the RPMI1640 containing 3% stripped fetal bovine serum and 2 mM glutamine. Cells were incubated at 37° C. in the humidifying incubator with 5% $CO_2$. 40 μL Cells were seeded (10000 cells/well) in medium contained in a 384-well Corning black transparent bottom plate, and incubated overnight at 37° C. under 5% $CO_2$. Acoustically dosed with Echo555, the continuously diluted compound in 100% DMSO was added to the cells. After the cells were incubated for 2 h, mixed with the medium gently, 40 μL lysis buffer was added to each well. The 384-well high cohesion black Greiner plate were covered with capture antibody, and then blocked with 3% BSA. Then the blocking liquid was removed, 15 lysis buffer was transferred to 384-well high cohesion black Greiner plate, incubated for 2 h, gently mixed and washed with PBS, 20 μL antibody was added, incubated for 2 h, gently mixed and washed with PBS, 20 μL QuantaBlu fluorescent peroxidase substrate (Thermo Fisher Scientific) was added and incubated for 1 h. 20 μL terminating solution of QuantaBlu was added to the plate, and the fluorescence was read by Envision microplate detector which employed an excitation wavelength of 352 nm and an emission wavelength of 460 nm. The obtained data of the compounds to be tested were input into the appropriate software package to perform curve fitting analysis. $IC_{50}$ value was determined by calculating the concentration of the compound when 50% effect was acquired based on these data.

The data obtained from the embodiments in the present application was shown in the table below. Although a certain number of valid numbers was used to express the tested data, it should not be understood that the data were precise to these valid numbers.

TABLE 1

$IC_{50}$ values of compounds obtained in Test 1 to 3

| Embodiment No. | Test 1 | Test 2 | Test 3 |
|---|---|---|---|
| 1B | 0.01973 | 0.01270 | 6.533** |
| 2B | 0.01974 | 0.01269 | 8.500** |
| 3B | 0.01961 | 0.01175 | 2.532* |
| 4B | 0.01988 | 0.01299 | 4.498* |
| 5B | 0.01971 | 0.01271 | 5.535* |
| 6B | 0.01991 | 0.01338 | 3.253* |
| AZD9291 | 0.01975 | 0.01271 | 1.443 |

Compare the embodiments with the control group,
*P < 0.05 represented significant difference between groups;
**P < 0.01 represented extremely significant difference between groups.

The results showed that all the embodiment compounds and control drug AZD9291 had activities on single mutant and double mutant cells; the embodiment compounds had better selectivity on wild-type EGFR cells, and achieved significant progress relative to the prior art.

Test 4: Evaluation of Stability of Compounds in Human Liver Microsomes

The stability of the compounds prepared according to embodiments 1B to 6B were compared with that of AZD9291 in the liver microsomes.

Assay system: the metabolic stability of the compounds in the present invention were determined by employing a mixture of male and female liver microsomes (Jiangyin Qi Biotechnology Co., Ltd.) and 1 mM NADPH. Samples were analyzed by a mass spectrometer. HRMS was used to determine the peak area response ratio (corresponding to the peak area of the compound to be tested or control compound being divided by the peak area of the internal standard) without running the standard curve. In order to detect all possible metabolites, HRMS scan were performed within an appropriate m/z range.

Determination condition: the assay was performed with one time incubation (N=1). The compounds to be tested were incubated at 37° C. in a PBS buffer containing 0.5 mg/mL liver microsomal protein. The reaction was initiated by adding cofactor NADPH (Roche), and sampled at 0, 8, 16, 24, 32, 48 h, the positive control (5 μM testosterone, Aladdin) was incubated in parallel and sampled at 0, 8, 16, 24, 32, 48 h.

Determination quality control: compare the testosterone of control compound in parallel to determine the enzyme detergent of (liver) microsomes. After the last time point, NADPH was added to the reaction mixture and detected by fluorimetry. $T_{1/2}$ of control compound met the acceptable internal standard.

Analysis Method:

Liquid chromatography column: Thermo BDS Hypersil C18 30×2.0 mm, 3 with a protective column M. P., buffer: 25 mM ammonium formate buffer, pH 3.5;

Aqueous phase (A): 90% water, 10% buffer;
Organic phase (B): 90% acetonitrile, 10% buffer;
Flow rate: 300 μL/min
Autosampler: injection volume 10 μL
Gradient program:

| Time (min) | % A | % B |
|---|---|---|
| 0.0 | 100 | 0 |
| 1.5 | 0 | 100 |
| 2.0 | 0 | 100 |
| 2.1 | 100 | 0 |
| 3.5 | 100 | 0 |

The stability in human liver microsomes were as follows:

| Compounds | Remaining Percentage (%) | | | | | | Half-time period |
|---|---|---|---|---|---|---|---|
| | 0 h | 8 h | 16 h | 24 h | 32 h | 48 h | |
| embodiment 1B | 100 | 93 | 86 | 77 | 70 | 67 | >48 h |
| embodiment 2B | 100 | 97 | 90 | 82 | 75 | 81 | >48 h |
| embodiment 3B | 100 | 90 | 82 | 73 | 64 | 55 | >48 h |
| embodiment 4B | 100 | 89 | 81 | 72 | 63 | 51 | >48 h |
| embodiment 5B | 100 | 91 | 84 | 75 | 69 | 66 | >48 h |
| embodiment 6B | 100 | 92 | 80 | 76 | 65 | 58 | >48 h |
| AZD9291 | 100 | 82 | 61 | 48 | 34 | 14 | 24 h |

The results showed that, compared with the control compound AZD9291, the half-life period of the compounds in the present invention were 48 h or longer (the half-life period of AZD9291 was 24 h), which promised a lower medical dose and longer dosing interval.

Test 5: Effect Assess in Nude Mice Implanted with NCI-H1975

To nude mice implanted with NCI-H1975, was administered 3.6 μgig (compound/nude mice weight) once a day in one group, and 7.2 μgig once a day in another group, and the tumor size was observed after continuous administration for 10 days.

| Embodiment | Dose 7.2 μg/g tumor size | | Dose 3.6 μg/g tumor size | |
|---|---|---|---|---|
| No. | 0 d | 11<sup>th</sup> d | 0 d | 11<sup>th</sup> d |
| 1B | 13 mm | 5 mm | 12 mm | 6 mm |
| 2B | 12 mm | 4 mm | 12 mm | 5 mm |
| 3B | 13 mm | 7 mm | 14 mm | 9 mm |
| 4B | 11 mm | 6 mm | 13 mm | 8 mm |
| 5B | 14 mm | 8 mm | 11 mm | 10 mm |
| AZD9291 | 12 mm | 8 mm | 13 mm | 13 mm |

The experimental results showed that the embodiment compounds had better inhibitory effect on tumor growth than AZD9291 under high dose. AZD9291 had very low inhibitory effect on tumor growth under low dose, the inhibitory activity on tumor growth of embodiment compounds were obviously promoted under low dose compared with that of AZD9291.

Test 6:

Tumor-bearing nude mice were divided into two groups, three for each group (female mice), administered with compound 3B and AZD9291, continuously dosed at 10 mg/kg/Day for 10 days, fed food and water in a common manner, administered by intragastric administration. The results of assay on inhibiting tumor growth were shown in FIG. 1.

Effect Embodiment 2

Main instruments and equipment required for the test

| Equipment name | Manufacturer | Model |
|---|---|---|
| LC/MS/MS | America AB/Japan Shimadzu | API4000+/LC-20AD |
| Centrifugal machine | Sorvall | Biofuge Stratos |
| Electronic balance | Japan Shimadzu | AUW120D |

2. Experimental Method 2.1. Grouping of Experimental Animals:

24 SD rats were half male and half female, randomly divided into 4 groups, 6 rats in each group, half male and half female Each group was: (1) the intragastric administration group to be tested (compound 3B) NO. 1-3 male, NO. 4-6 female
 (2) the control intragastric administration group (AZD9291) NO. 7-9 male, NO. 10-12 female 2.2. Experimental Reagents and Administration Modes
Intragastric Administration:

25 mg/kg compound 3B was formulated into a 5 mg/mL solution, dissolved in normal saline, about 10 mL, and prepared when it was ready to use.

25 mg/kg AZD9291 was prepared into a 5 mg/mL solution, dissolved in normal saline, about 10 mL, and prepared when it was ready to use.

2.3. Test Steps 1. the rats were fed for one week for adaption and fasted for 12 h before administration;

2. grouping and weighing rats;

3. compound 3B and AZD-9291 were administrated respectively by intragastric administration, 25 mg/kg, 200 μL orbital blood was sampled at 15 min, 30 min, 1 h, 2 h, 3 h, 4 h, 6 h, 8 h, 12 h, 24 h, 36 h, 48 h, 72 h, 96 h;

4. the blood samples were centrifuged, supernatant was extracted, treated, and analyzed. Test results were shown in FIG. 2 and FIG. 3.

Figure 2:
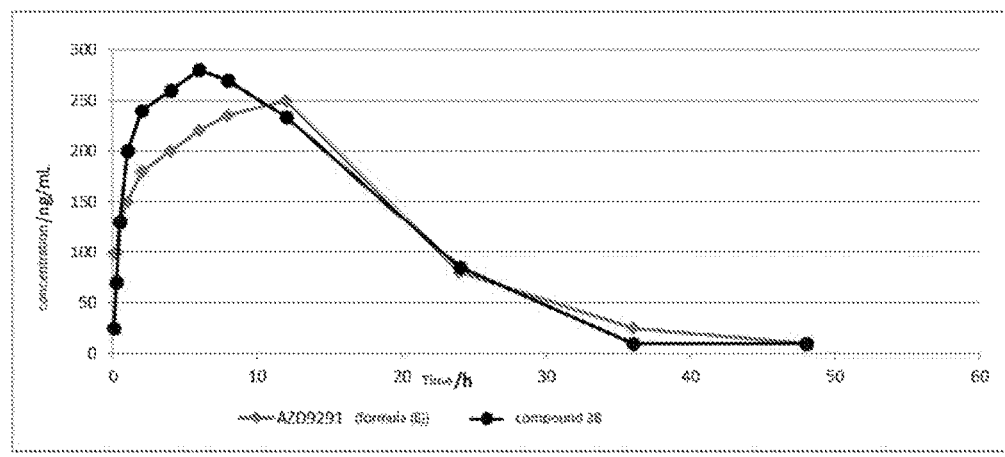
FIG. 2 is the mean drug concentration-time curve (n=6) of AZD9291 (formula (II)) and embodiment compound 3B administered at 25 mg/kg after intragastric administration.
Figure 3:
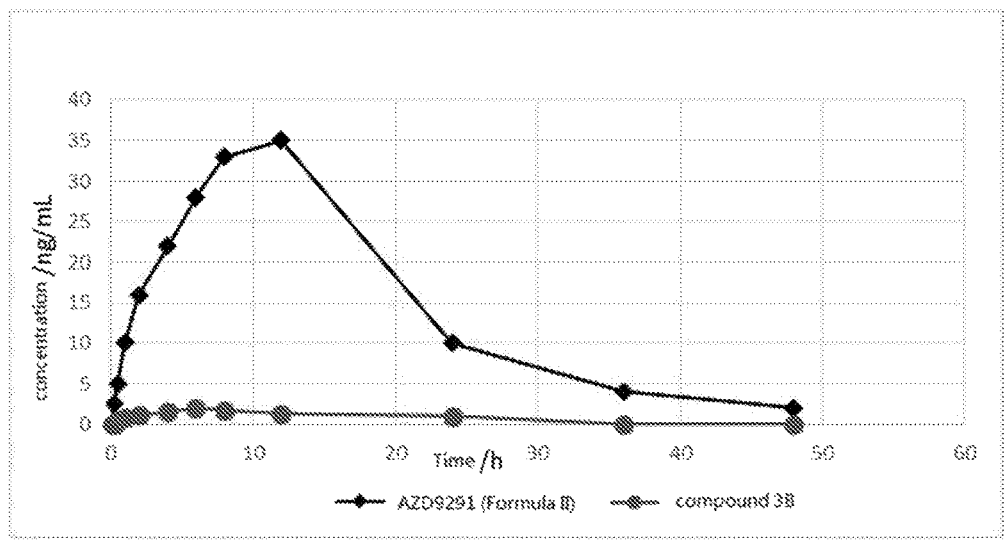
FIG. 3 is the mean drug concentration-time curve (n=6) of the metabolite which is derived from the demethylation of indole in rats administered by AZD9291 and embodiment compound 3B at 25 mg/kg after intragastric administration.

FIG. 2 showed that compound 3B of the present invention had better pharmacokinetics, that was, the compounds of the present invention could reach a higher level of blood concentration within shorter time, and the blood concentration could be maintained at a higher level for a relatively long time, which reflected the compounds of the present invention had higher permeability and more excellent in vivo stability. FIG. 3 showed that compared with the control drug, the compounds of the present invention had less metabolites over the same period, reduced the burden of the liver and toxic side effects of the drugs, and had lasting effect.

For a person skilled in the art, the disclosure is not limited to the foregoing illustrative examples, and can be embodied in other specific forms without the need for its essential attributes. So it's expected that all respects are illustrative but not restrictive, the claims attached for reference instead of the embodiment of the aforementioned embodiments, references only aim for additional claims rather than the above embodiments, and all changes falling into the scope of equivalent meaning and range of the claims are therefore expected to include this.

All of the patents, patent applications and references cited in this specification are incorporated herein as a reference. In the case of inconsistency, the public text including the definition will be convincing.

Although the above text described embodiments of the present invention, but a person skilled in the art should understand that these are only examples, in the premise of not deviating from the principle and essence of the present invention, variety of changes or modifications can made to these embodiments. Therefore, the protection scope of the present invention is limited by the attached claims.

What is claimed is:

1. A 2-(2,4,5-substituted aniline)pyrimidine derivative, solvate, or pharmaceutically acceptable salt thereof selected from the group consisting of N-(2-{2-dimethylaminoethyl-methylamino}-4-methoxy-5-{[4-(1-(D$_3$-methyl)indol-3-yl)pyrimidin-2-yl]amino}phenyl)-2-acrylamide;

N-(2-{2-dimethylaminoethyl-methylamino}-4-(D$_3$-methoxy)-5-{[4-(1-methylindol-3-yl)pyrimidin-2-yl]amino}phenyl)-2-acrylamide;

N-(2-{2-dimethylaminoethyl-(D$_3$-methyl)amino}-4-methoxy-5-{[4-(1-methylindol-3-yl)pyrimidin-2-yl]amino}phenyl)-2-acrylamide;

N-(2-{2-di(D$_3$-methyl)aminoethyl-methylamino}-4-methoxy-5-{[4-(1-methylindol-3-yl)pyrimidin-2-yl]amino}phenyl)-2-acrylamide; and N-(2-{2-[methyl(D$_3$-methyl)amino]ethyl-methylamino}-4-methoxy-5-{[4-(1-methylindol-3-yl)pyrimidin-2-yl]amino}phenyl)-2-acrylamid, wherein the D$_3$-methyl or D$_3$-methoxy substituents comprise deuterium at a percentage higher than the natural abundance of deuterium.

2. The 2-(2,4,5-substituted aniline)pyrimidine derivative, solvate, or pharmaceutically acceptable salt thereof according to claim 1, wherein the pharmaceutically acceptable salt includes a salt of an inorganic acid and a salt of an organic acid; the salt of the inorganic acid being hydrochloride, hydrobromide, hydriodate, sulfate, phosphate, or a salt of hydrogen disulfide; the salt of the organic acid being p-toluene sulfonate, salicylate, tartrate, hydrogen tartrate, ascorbate, maleate, benzene sulfonate, fumarate, gluconate, glucuronate, formate, glutamate, mesylate, esylate, benzene sulfonate, lactate, oxalate, brosylate, carbonate, citrate, benzoate, malate or acetate.

3. A method for treating lung cancer in a subject in need thereof, the method comprising administering an effective amount of the 2-(2,4,5-substituted aniline)pyrimidine derivative, solvate, or pharmaceutically acceptable salt thereof according to claim 1, to the subject.

4. The method according to claim 3, wherein the lung cancer is non small-cell lung cancer.

\* \* \* \* \*